(12) United States Patent
Davis et al.

(10) Patent No.: US 11,123,054 B2
(45) Date of Patent: *Sep. 21, 2021

(54) MOUNTING CLAMP FOR AN ILLUMINATED SURGICAL RETRACTOR SYSTEM

(71) Applicant: Sunoptic Technologies, LLC, Jacksonville, FL (US)

(72) Inventors: James M. Davis, Naples, FL (US); Kim A. Marsh, Naples, FL (US)

(73) Assignee: Sunoptic Technologies, LLC, Jacksonville, FL (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/949,654

(22) Filed: Apr. 10, 2018

(65) Prior Publication Data
US 2018/0296204 A1   Oct. 18, 2018

Related U.S. Application Data

(60) Provisional application No. 62/485,530, filed on Apr. 14, 2017.

(51) Int. Cl.
| A61B 17/02 | (2006.01) |
|---|---|
| A61B 1/06 | (2006.01) |
| A61B 90/30 | (2016.01) |
| A61B 1/07 | (2006.01) |
| A61B 1/32 | (2006.01) |

(52) U.S. Cl.
CPC ........ A61B 17/0206 (2013.01); A61B 1/0615 (2013.01); A61B 17/02 (2013.01); A61B 90/30 (2016.02); *A61B 1/07* (2013.01); *A61B 1/32* (2013.01); *A61B 17/0218* (2013.01); *A61B 2090/306* (2016.02)

(58) Field of Classification Search
CPC . A61B 17/02; A61B 17/0206; A61B 17/0218; A61B 90/30; A61B 1/0615
USPC .......................... 600/227–230; 606/246–279
See application file for complete search history.

(56) References Cited

U.S. PATENT DOCUMENTS

| 6,322,499 B1 * | 11/2001 | Evans ............. A61B 17/00008 |
| | | 600/210 |
| 2017/0273846 A1 * | 9/2017 | Yancey ................ A61G 13/101 |

* cited by examiner

*Primary Examiner* — Si Ming Ku
(74) *Attorney, Agent, or Firm* — William E. Noonan

(57) ABSTRACT

A mounting clamp is disclosed for an illuminated surgical retractor system having a handle that supports an illuminated surgical retractor blade. The mounting clamp is attached to and depends from the handle. The mounting clamp includes a receptacle for receiving a slide bar or other fixed component of an operating room table. The clamp further includes a fastener that is selectively tightened to secure the retractor assembly to the fixed component of the table. The fastener is selectively loosened to disengage the retractor assembly from the fixed component of the table.

11 Claims, 2 Drawing Sheets

MOUNTING CLAMP FOR AN ILLUMINATED SURGICAL RETRACTOR SYSTEM

RELATED APPLICATION

This application claims the benefit of U.S. Provisional Patent Application Ser. No. 62/485,530 filed Apr. 14, 2017.

FIELD OF THE INVENTION

This invention relates to an illuminated retractor system for use in medical and surgical procedures. More particularly, the invention relates to a mounting clamp for releasably attaching the retractor system to a slide bar of an operating table at a selected position along the slide bar.

BACKGROUND OF THE INVENTION

Surgical retractors are commonly used by surgeons to separate the edges of a surgical incision or wound. Such instruments are also utilized to restrain the organs and tissues of a patient undergoing surgery so that body parts under the surgical incision may be more readily accessed. Most retractors employ one or more curved, hooked or angled steel blades attached to a handle that is manipulated during surgery by the surgeon or other medical personnel.

Recently, surgical retractors have been improved by the use of lighting systems that are mounted to the retractor blades. In such products, a light projecting element is typically attached to the blade and light is supplied to that element by a fiberoptic illuminator and interconnected fiberoptic cable. Such lighting systems illuminate the surgical site so that surgery is facilitated and improved surgical results are achieved.

Conventional illuminated surgical retractors exhibit various drawbacks. Most such systems are not very versatile. Different types of surgery and patients having differing physical features may require the use of various sizes, and shapes of retractors for respective applications. The hospital or other surgical facility must therefore maintain a large number of differently sized and configured retractor systems, which can be quite costly. By the same token, conventional surgical retractors are typically constructed as an integrated system wherein the fiberoptic cable, handle, blade and light carrier Bare are not practically separable or interchangeable. As a result, if a single one of these components fails, the entire retractor system must be replaced. This is not only expensive, it can also cause an inconvenient and potentially dangerous delay during a time sensitive surgical procedure.

Conventional illuminated retractors can also be awkward to manipulate and difficult to properly position and hold securely in place so that optimum surgical lighting is provided. Indeed, a great need exists for a surgical lighting system that not only effectively retracts surgical incisions and restrains organs and tissues, but also better illuminates the surgical site so that improved surgical results are achieved.

Our co-pending patent application Ser. No. 14/880,632 (hereinafter Ser. No. '632) discloses an illuminated surgical retractor system including a handle that supports an interchangeable illuminated retractor blade. An optical coupler within a channel of the handle interconnects the retractor blade to a light carrier. This tool is intended to be manually held by the surgeon or other medical professional during surgery. However, in some cases, it may be necessary or desirable to secure the retractor system to the operating room table or surrounding structure.

SUMMARY OF THE INVENTION

It is therefore an object of the present invention to provide an illuminated surgical retractor system featuring a mounting clamp that allows the retractor system to be quickly, conveniently and reliably secured to an operating table slide bar or other structure adjoining the table so that the retractor may be held securely in place during a surgical procedure.

It is a further object of this invention to provide a mounting clamp for an illuminated surgical retractor system that permits the retractor system to be positionally adjusted in a quick, convenient and effective manner so that the retractor may be used more effectively during surgery.

It is a further object of this invention to provide a mounting clamp for an illuminated surgical retractor system that enables the retractor to be used effectively without having to be manually held by a physician or other medical personnel during a surgical procedure and which therefore allows that person to more effectively and efficiently participate in the procedure.

This invention features a surgical retractor system including a retractor blade and a light carrier supported by the retractor blade and composed of a solid and preferably one-piece light conducting and projecting material. The retractor blade is connected to an elongate handle such that the light carrier and a fiberoptic cable can be optically coupled within the handle. A mounting clamp is attached to and depends from the handle. The mounting clamp is positionally adjustable along and releasably connectable to an elongate structural component attached to the operating room table. The clamp is closed at a selected position along the elongate structural component to secure the retractor system to the table.

In a preferred embodiment, the clamp includes a receptacle for engaging the elongate structural component attached to the table. The elongate structural component may include a slide bar mounted to the operating room table. A set screw assembly may be operatively mounted within a corresponding threaded hole of the clamp, Closing the set screw of the clamp causes an inner end of the set screw to engage the slide bar such that the clamp secures the retractor system in a selected position along the slide bar. Alternatively, opening the set screw disengages the set screw from the slide bar and allows the position of the clamp and retractor system to be adjusted longitudinally on the slide bar.

In a preferred embodiment, the mounting clamp may include an upper end that directly engages and supports the handle, and an opposite lower end. The mounting clamp may further include leading and trailing ends that interconnect the upper and lower ends of the mounting clamp. The slide bar receptacle may be formed through one of the leading and trailing ends. The receptacle may include a concave inner end for conformably engaging a slide bar that is inserted into the slide bar receptacle. The set screw accommodating hole may interconnect the lower end of the mounting clamp and the slide bar receptacle such that a set screw accommodated within the hole may be selectively tightened to engage a slide bar accommodated in the receptacle of the mounting clamp. This secures the clamp and retractor system to the slide bar.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
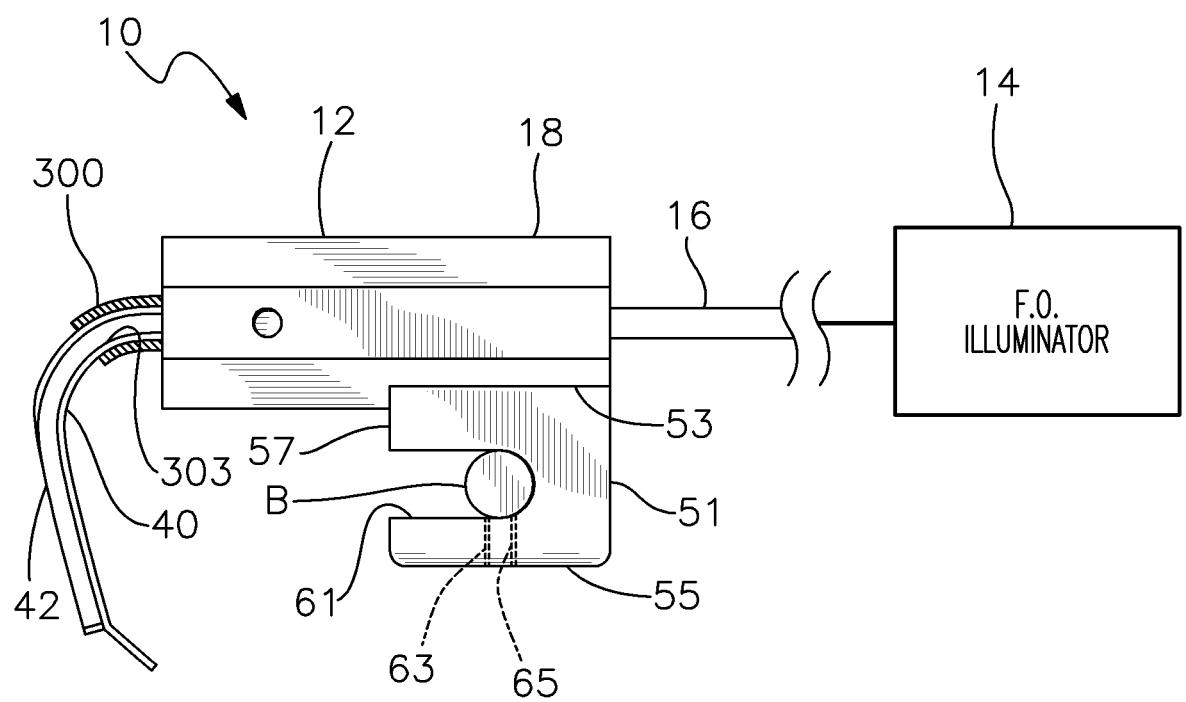
FIG. 1 is a side elevational view of a surgical illuminator system, which includes a mounting clamp for securing the system to a slide bar of an operating room table in accordance with this invention.

There is shown in FIG. 1 an illuminated surgical retractor system 10, which is intended for use during surgical and medical procedures. For example, system 10 may be used effectively for various types of plastic surgery including but not limited to breast augmentation. The system is also extremely effective for use in virtually all types of thoracic surgery involving the chest or abdomen wherein the edges of a surgical incision must be separated and/or tissue, muscles and internal organs must be constrained and the surgical site illuminated. It should be understood that the specific medical and surgical applications for which system 10 may be used are not a limitation of this invention.

Illuminated retractor system 10 includes a retractor apparatus 12 that is interconnected to a standard fiberoptic illuminator 14 by a fiberoptic cable 16. Various types of fiberoptic illuminators, which are either conventional or to be developed may be employed within the scope of this invention. The light source may include, without limitation, neon, xenon and any and all various other types of light source. The fiberoptic cable typically includes multiple strands of optical fibers constructed in a conventional manner.

Figure 2:
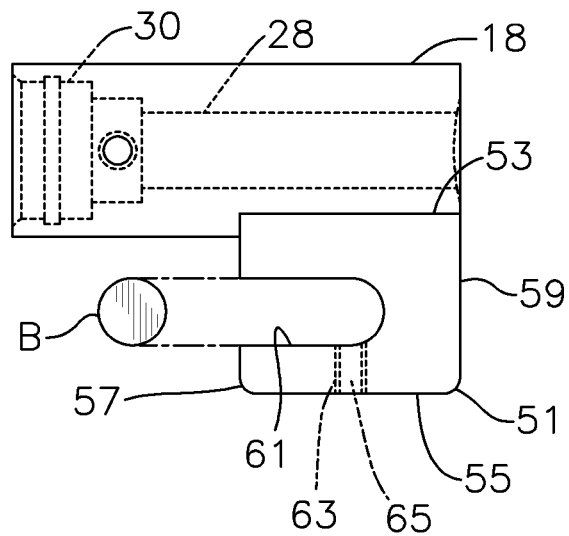
FIG. 2 is side elevational view of the retractor handle and attached mounting clamp with the internal channels and set screw holes depicted in phantom; the mounting clamp is positioned adjacent to the slide bar of the operating room table.
Figure 3:
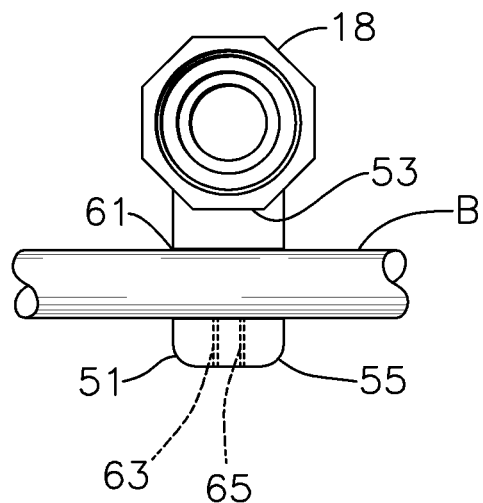
FIG. 3 is a front elevational view of the retractor handle and attached mounting clamp positioned on the slide bar.
Figure 4:
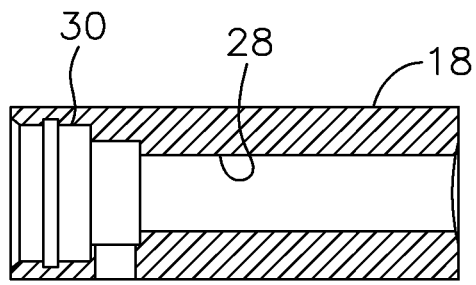
FIG. 4 is a top cross sectional view of the handle.

Retractor apparatus 12 includes a handle 18, which is further depicted in FIGS. 2-4. Handle 18 supports a stainless steel retractor blade assembly 40 and a light conducting and projecting carrier component 42 that is supported by blade assembly. More particularly, handle 18 supports blade 40 and light carrier 42 such that the light carrier is optically coupled to an outlet end of fiberoptic cable 16. The structure for accomplishing such optical coupling is disclosed in our pending U.S. patent application Ser. No. 14/880,632 filed Oct. 12, 2015 and published on Apr. 14, 2016, Publication No. US-2016-0100751. The disclosure contained therein is incorporated herein by reference. More particularly, an optical coupler as described in Ser. No. '632 interconnects blade 40 and carrier 42 with an inner end of fiberoptic cable 16. Handle 18 includes an interior channel 28, FIGS. 2 and 4, and a receptacle 30 that accommodate the fiberoptic cable 16, as well as the mounting assembly of the retractor blade 40 and the inlet end of light carrier 42, in the manner described in Ser. No. '632.

Rod portion 303 of blade 40 may optionally include a thickened sheathing 300 comprising silicone USP Class IV medical grade plastic or an alternate synthetic material. This forms an overmold for limiting light dispersion from the rod portion of the blade. As a result, light is delivered more efficiently through blade 40 and the surgeon or other user is less likely to be distracted by light dispersed from rod portion 303. See also pending application Ser. No. 15/172, 764, the description of which is also incorporated by reference herein.

The illuminated surgical retractor disclosed in Ser. No. '632 is a handheld device and the handle described therein is constructed and configured in order to be manually manipulated by a physician or other medical personnel involved in a surgical or medical procedure. In the present invention, retractor apparatus 12 is designed to be fixedly mounted on a slide bar B, FIGS. 1-3, which is itself mounted to the operating table (not shown) on which the surgical or medical procedure is being performed. Handle 18 includes a cylindrical or polygonal exterior surface. The finger grippable undulations depicted in the handle described in Ser. No. '632 are not employed in the present version. Instead, handle 18 and retractor apparatus 12 are securely fastened at a desired position along slide bar B. This is accomplished by means of a mounting clamp 51, which is attached to and depends from handle 18.

In particular, mounting clamp 51 includes an upper end 53 and a lower end 55 as depicted in FIG. 3. A leading end 57 of mounting clamp 51 faces in a direction generally forwardly of the handle. A trailing end 59 of clamp 51 faces rearwardly and is positioned proximate an inlet end of the handle. Both ends 57 and 59 interconnect the upper and lower ends 53 and 55 of mounting clamp 51. The mounting clamp typically comprises a durable metallic or synthetic material such as stainless steel or other medical grade material. Clamp 51 may be machined, molded, diecast or otherwise formed unitarily with handle 18. Alternatively, the mounting clamp may be permanently fixed to handle 18 by screws or any other acceptable means.

A slide bar accommodating receptacle 61 is formed in mounting clamp 51 and, more specifically, in and leading end 57 of clamp 51. As best shown in FIGS. 1 and 2, the interior end of receptacle 61 includes a concave shape that preferably conforms to the cross sectional shape of slide bar B such that mounting clamp 51 fits onto and engages the slide bar in a snug and secure manner at the interior end of the receptacle. A set screw accommodating hole 63 formed in the lower end 55 of mounting clamp communicates with receptacle 61. Hole 63 is threaded for operatively receiving a corresponding set screw 65. With receptacle 61 of mounting clamp 51 engaging slide bar B, set screw 65 may be tightened to secure the mounting clamp and retractor handle onto the slide bar.

In operation, an interchangeable light carrier and retractor blade are operatively interengaged with the fiberoptic illuminator (not shown) and attached cable 16 via handle 18. This is accomplished in a manner identical or analogous to that described in Ser. No. '632. The surgical retractor may then be quickly, conveniently and securely fixed to the operating table by engaging mounting clamp 51 with a slide bar B or other elongate support component attached to the operating table. The retractor assembly may be positioned longitudinally along the slide bar by sliding clamp 51 along bar B so that the bar effectively slides through receptacle 61. This enables the retractor assembly to be properly positioned for use during surgery or a medical procedure. When the proper positioning is achieved, set screw 65 is tightened within hole 63 to secure the retractor apparatus in place at the selected position along slide bar B.

The various components of retractor assembly 12, including the retractor blade 40, handle 18 and depending clamp 51 preferably comprise a strong and rigid metallic material such as surgical steel. Handle 18 and clamp 51 may be machined, molded or otherwise formed unitarily. Alternatively, the components may be formed separately and fastened together by screws, bolts or other means. Medical grade synthetic materials may also be employed for the clamp and handle.

The system of the present invention successfully allows many different sizes of retractor blades and illuminating light carriers to be interchanged and replaced as needed or desired in connection with different surgical procedures and patient requirements. In contrast to the prior art, if a single component of this system fails, the entire system does not have to be replaced. Only the defective component must be changed and needed repair or replacement can be performed quickly and conveniently. In addition, the hospital or other surgical facility does not have to maintain an unnecessarily large supply of expensive and possibly duplicate parts. Standard fiberoptic cables may be employed much more efficiently in connection with a number of variously sized retractor blades and light conducting/projecting carriers. By the same token, a single universal handle can be used with numerous combinations of retractor blades and illuminating light carriers. Medical and surgical costs are thereby reduced and much more efficient management of surgical supplies is achieved.

As indicated in Ser. No. '632, the retractor blade assembly and light carrier may have various different sizes, configurations and angles. Although generally flat, blade-like shapes are depicted herein, in other embodiments, the retractor blades and light projection portion of the light carrier may feature round or alternatively configured shapes.

The mounting clamp may likewise include different sizes and configurations. In addition, the bar accommodating receptacle 61 may have different shapes and dimensions, and may be positioned and oriented in various alternative ways within the clamp. For example, receptacle 61 may be formed in and extend forwardly from the trailing end 51 of the clamp. The receptacle may also be formed in and extend upwardly from bottom end 55 of clamp 51. In such versions, the orientation of the set screw and set screw receiving hole are changed accordingly to operatively engage the re-oriented slide bar receptacle. In this manner, the illuminated retractor assembly may be adjustably secured to a slide bar or other fixed component of an operating room table in a manner that best positions the retractor assembly for most effectively engaging a patient so that surgical retraction is successfully performed in the manner required for a particular surgical or medical procedure. The physician or other medical personnel's hands are thereby freed from having to hold the retractor and allowed to perform other tasks as may be required during the medical procedure.

In still other embodiments, the set screw may be replaced by other types of screws or fasteners that are selectively closed and opened to respectively close and open the clamp.

It should be understood that the retractor blade assembly 12, as well as the retractor blade assemblies disclosed in the co-pending applications referenced herein, may also be effectively supported by various other known clamps and holders used in the surgical and medical industries for supporting surgical retractors. In such cases, the user's hands are likewise freed from having to hold the illuminator retractor blade during surgery. The clamp 51 disclosed herein is especially effective for use in connection with the slide bar or other fixed structure of a surgical table.

In alternative embodiments, the slide bar may have other non-circular cross sectional shapes (e.g. square, rectangular, hexagonal, etc.) In such cases the set screw or other fastener engages a flat surface of the slide bar. The bar may feature other curved, non-circular cross sectional shapes (e.g. oval) within the scope of this invention.

Accordingly, the present invention relates to an improved illuminated retractor system featuring a mounting clamp for securing the retractor system to a slide bar or other fixed component of an operating room table. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. A surgical retractor system comprising:
   a retractor blade;
   a light carrier supported by said retractor blade and composed of a light conducting and projecting material said retractor blade and said light carrier being releasably connected to a handle having a straight interior channel formed longitudinally therethrough, said interior channel accommodating an optical coupler, which said optical coupler is releasably interengaged by said light carrier and an inner end of a fiberoptic cable to optically interconnect said fiberoptic cable to said light carrier within said interior channel, each of said light carrier and said fiberoptic cable being selectively disengageable from said optical coupler to detach said light carrier from said fiberoptic cable and remove said fiberoptic cable from said handle; said light carrier including a light inlet section received by and communicably and releasably interengaged with a female port of said optical coupler; said retractor blade being releasably interengaged with a receptacle formed in a leading end of said handle, said receptacle communicating with said interior channel; said interior channel being configured such that when said retractor blade is released from interengagement with said receptacle and said light inlet section of said light carrier is disengaged from said female output port of said optical coupler, said fiberoptic cable and said optical coupler interengaged with said cable are selectively movable longitudinally through said channel and said receptacle to extend said optical coupler beyond a distalmost end of said receptacle and said leading end of said handle; and
   a mounting clamp permanently and contiguously fixed to said handle, said mounting clamp being positionally adjustable on and releasably connectable to a supportive component attached to or proximate an operating room table; said mounting clamp being closed at a selected location on said supportive component to secure and restrict movement of the retractor system relative to the supportive component.

2. The system of claim 1 in which said mounting clamp includes a receptacle for engaging said supportive component.

3. The system of claim 2 in which the supportive component includes an elongate slide bar mounted to the operating room table.

4. The system of claim 3 in which a set screw is operatively mounted within a corresponding threaded hole of said mounting clamp such that closing said set screw assembly causes an inner end of said set screw to engage the slide bar such that said mounting clamp secures the retracting system in a selected position along the slide bar and opening said set screw disengages said set screw from the slide bar and allows the position of said mounting clamp to be adjusted longitudinally on the slide bar.

5. The system of claim 1 in which said mounting clamp includes an upper end that directly engages, is contiguous with and supports said handle above said clamp, and an opposite lower end.

6. The system of claim 5 in which said mounting clamp further includes leading and trailing ends that interconnect said upper and lower ends of said mounting clamp, said receptacle being elongate and formed through one of said leading and trailing ends and generally parallel to a longitudinal axis of said interior channel.

7. The system of claim 2 in which said receptacle includes a concave inner end for conformably engaging the slide bar when the slide bar is inserted into said receptacle.

8. The system of claim 5 in which a set screw accommodating hole interconnects said lower end of said mounting clamp and a receptacle and further including a set screw accommodated within said set screw accommodating hole, which set screw is selectively tightened to engage a slide bar received by said receptacle, which secures said clamp and said retractor system to the slide bar.

9. The system of claim 1 in which said handle is elongate and said interior channel extends longitudinally through said handle.

10. An illuminated surgical retractor system for use with a fiberoptic illuminator, said system comprising:
    a light conducting fiberoptic cable that is attachable at a light input end thereof to the fiberoptic illuminator, said fiberoptic cable having an opposite light output end for discharging illumination produced by the fiberoptic illuminator therefrom;
    an elongate handle having a straight channel formed longitudinally therethrough for receiving said light output end of said light conducting fiberoptic cable and permitting said fiberoptic cable to move longitudinally through said channel to selectively maintain said light output end of said cable at a position proximate a leading end of said handle;
    a light carrier composed of a light conducting and projecting material;
    a retractor blade assembly releasably interengaged with a receptacle formed in said leading end of said handle and in communication with said channel of said handle, said retractor blade assembly including a mounting collar received by said receptacle of said handle, said mounting collar having an interior slot for removably receiving said light carrier such that a light inlet end of said light carrier extends from said mounting collar and is releasably interengageable and optically communicable with said light output end of said fiberoptic cable within said handle; said retractor blade assembly also including a retractor blade and a holder section interconnecting said mounting collar and said retractor blade, said holder section having a conduit for accommodating an intermediate light transmitting portion of said light carrier therein; and a light projecting portion of said light carrier engaging and being secured to said retractor blade; whereby the fiberoptic illuminator is operable to transmit light through said fiberoptic cable and to said light carrier such that said light projecting portion of said light carrier projects light onto a surgical site with which said retractor blade is engaged, said channel being configured such that when said retractor blade is released from interengagement with said receptacle and said light inlet section of said light carrier is released from interengagement with said light output end of said fiberoptic cable, said fiberoptic cable is freely movable longitudinally through said channel and said receptacle to selectively extend said light output end of said fiberoptic cable beyond a distal most end of said receptacle and said leading end of said handle; and
    a mounting clamp permanently and contiguously fixed to said handle, said mounting clamp being positionally adjustable on and releasably connectable to a supportive component attached to or proximate an operating room table; said mounting clamp being closed at a selected location on said supportive component to secure and restrict movement of the retractor system relative to the supportive component.

11. An illuminated surgical retractor system for use in combination with a fiberoptic illuminator and light conducting fiberoptic cable attached at a light input end thereof to the fiberoptic illuminator, said system comprising:
    an elongate handle having a straight channel formed longitudinally therethrough and extending from a trailing end of said handle for receiving a light output end of said fiberoptic cable and permitting said fiberoptic cable to selectively move longitudinally through said channel;
    an optical coupler receivable within said channel, said optical coupler having inlet and outlet ports and an interior bore that communicably interconnects said inlet and outlet ports, said inlet port, for being communicably and releasably interengaged by a light output end of said fiberoptic cable;
    a retractor blade assembly releasably interengaged with a receptacle formed in a leading end of said handle, said receptacle communicating with said channel formed through said handle;
    a light carrier for attaching to said retractor blade assembly, said light carrier including a light inlet section that is communicably and releasably interengageable with said outlet port of said optical coupler and a light projecting portion communicably connected to said light inlet section, the fiberoptic illuminator being operable to transmit light through the fiberoptic cable and through said optical coupler to said light inlet section of said light carrier such that said light projecting portion of said light carrier projects light onto a surgical site with which said retractor blade assembly is engaged;
    said channel being configured such that the fiberoptic cable and said interengaged optical coupler are axially rotatable within said channel and, when said retractor blade assembly is released from interengagement with said receptacle and said light inlet section of said light carrier is released from interengagement with said outlet port of said optical coupler, said fiberoptic cable and said interengaged optical coupler are selectively movable longitudinally fully through said channel and said receptacle to extend said optical coupler beyond a distalmost end of said receptacle and said leading end of said handle; and
    a mounting clamp permanently and contiguously fixed to said handle, said mounting clamp being positionally adjustable on and releasably connectable to a supportive component attached to or proximate an operating room table; said mounting clamp being closed at a selected location on said supportive component to secure and restrict movement of the retractor system relative to the supportive component.

* * * * *